United States Patent
Sato (10) Patent No.: US 10,058,304 B2
(45) Date of Patent: Aug. 28, 2018

(54) BIOLOGICAL SIGNAL DETECTION DEVICE

(71) Applicants: KYUSHU INSTITUTE OF TECHNOLOGY, Kitakyushu-shi, Fukuoka (JP); AI TECHNOLOGY INC., Fukuoka-shi, Fukuoka (JP)

(72) Inventor: Yasushi Sato, Kitakyushu (JP)

(73) Assignees: KYUSHU INSTITUTE OF TECHNOLOGY, Fukuoka (JP); AI TECHNOLOGY INC., Fukuoka (JP)

( * ) Notice: Subject to any disclaimer, the term of this patent is extended or adjusted under 35 U.S.C. 154(b) by 0 days.

(21) Appl. No.: 15/560,729

(22) PCT Filed: Mar. 17, 2016

(86) PCT No.: PCT/JP2016/058604
§ 371 (c)(1),
(2) Date: Sep. 22, 2017

(87) PCT Pub. No.: WO2016/152742
PCT Pub. Date: Sep. 29, 2016

(65) Prior Publication Data
US 2018/0070919 A1    Mar. 15, 2018

(30) Foreign Application Priority Data
Mar. 23, 2015  (JP) .................................. 2015-059283

(51) Int. Cl.
*G06F 15/00*     (2006.01)
*A61B 8/00*      (2006.01)
(Continued)

(52) U.S. Cl.
CPC ............ *A61B 8/4416* (2013.01); *A61B 5/053* (2013.01); *A61B 5/6893* (2013.01);
(Continued)

(58) Field of Classification Search
USPC ......................................................... 708/404
See application file for complete search history.

(56) References Cited

U.S. PATENT DOCUMENTS 6,519,372 B1 * 2/2003 Eppler ................. G06K 9/6203
382/278

FOREIGN PATENT DOCUMENTS

| JP | 2004-125399 A | 4/2004 |
| JP | 2008-058470 A | 3/2008 |

(Continued)

OTHER PUBLICATIONS

Jun. 1, 2016 Search Report issued in Internatinal Patent Application No. PCT/JP2016/058604.

*Primary Examiner* — Tan V. Mai
(74) *Attorney, Agent, or Firm* — Oliff PLC (57) ABSTRACT

A biological signal detection device including a first FFT transformer that performs fast Fourier transformation on a signal of a first sensor, and that outputs a complex data row formed by a first real part data row and a first imaginary part data row; a second FFT transformer that performs fast Fourier transformation on a signal of a second sensor, and that outputs a complex data row formed by a second real part data row and a second imaginary part data row; a frequency component subtractor that subtracts the first real part data row from the second real part data row to output a noise-removed first real part data row; and a FFT inverse transformer that performs fast Fourier inverse transformation on the noise-removed first real part data row and the second imaginary part data row.

2 Claims, 7 Drawing Sheets

(51) Int. Cl.
*A61B 5/00* (2006.01)
*A61B 8/08* (2006.01)
*A61B 8/02* (2006.01)
*A61B 5/053* (2006.01)

(52) U.S. Cl.
CPC .............. *A61B 5/7257* (2013.01); *A61B 8/02* (2013.01); *A61B 8/488* (2013.01); *A61B 8/5269* (2013.01); *A61B 2503/08* (2013.01)

(56) References Cited

FOREIGN PATENT DOCUMENTS

WO 02/50814 A1 6/2002
WO 2014/084162 A1 6/2014

* cited by examiner

BIOLOGICAL SIGNAL DETECTION DEVICE

Technical Field

The present invention relates to a biological signal detection device adapted to detect a biological signal having periodicity.

BACKGROUND ART

To detect the pulse of a human body, it is conventionally necessary to bring a sensor into contact with the human body, such as detecting the pulse of the human body with a photoelectric pulse sensor or an ECG machine.

If the pulse of a human body can be detected in a non-contact manner, such technique will be expected to be applied to products for health maintenance and health management, application to watching over and sensing elderly people living alone and the like.

CITATION LIST

Patent Literature

Patent Document 1: Japanese Unexamined Patent Application Publication No. 2004-125399

SUMMARY OF INVENTION

Technical Problem

Almost all commercially available Doppler sensors, including the Doppler sensor disclosed in Patent Document 1, have the function of detecting approaching or moving away of a human being, but do not have a resolution high enough to detect the cardiopulmonary function of a human being.

Since conventional Doppler sensors use a radio wave having a frequency in UHF (Ultra High Frequency) band, the inventor of the present application lowers the frequency of the radio wave to a frequency in VHF (Very High Frequency) band to thereby achieve a sensor having improved signal processing. With such a configuration, it becomes possible to achieve a sensor having a resolution high enough to detect the cardiopulmonary function of a human being; however, since the detectable distance is short, if the distance between an object-to-be-detected and the sensor increases, noise will be easily picked up.

The present invention is made to solve the aforesaid problems, and it is an object of the present invention to provide a biological signal detection device which can detect low-frequency vibration of an object-to-be-detected (such as pulse of a human body) in a non-contact manner, and properly remove noise.

Solution to Problem

To solve the aforesaid problems, a biological signal detection device according to an aspect of the present invention includes: a first FFT transformer that performs fast Fourier transformation on a signal of a first sensor, and that outputs a complex data row formed by a first real part data row and a first imaginary part data row; a second FFT transformer that performs fast Fourier transformation on a signal of a second sensor, and that outputs a complex data row formed by a second real part data row and a second imaginary part data row; a frequency component subtractor that subtracts the first real part data row from the second real part data row to output a noise-removed first real part data row; and a FFT inverse transformer that performs fast Fourier inverse transformation on the noise-removed first real part data row and the second imaginary part data row

Advantageous Effects of Invention

According to the present invention, it is possible to provide a biological signal detection device which can detect low-frequency vibration of an object-to-be-detected (such as the pulse of a human body) in a non-contact manner, and properly remove noise.

Other problems, configurations and effects than those described above will be made clear by the description of the following embodiment.

DESCRIPTION OF EMBODIMENTS

[Operation Principle of Biological Signal Detection Device 104]

Figure 1A:
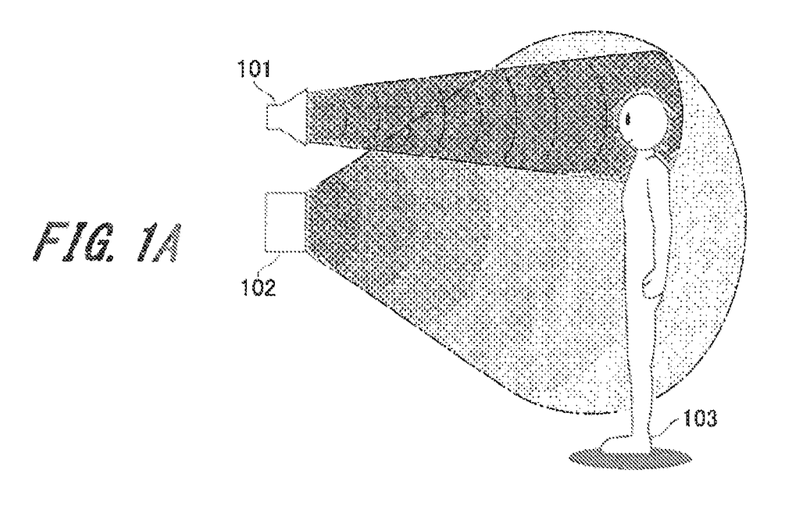
FIG. 1A is schematic view showing a range possible to be detected by a Doppler sensor and a range possible to be detected by an electric field-type sensor.

FIG. 1A is a schematic view showing a range possible to be detected by a Doppler sensor 101 and a range possible to be detected by an electric field-type sensor 102.

Figure 1B:
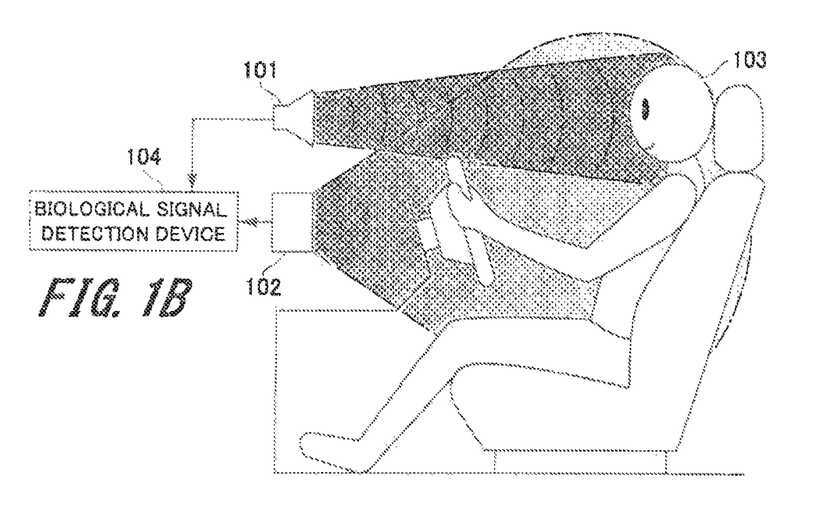
FIG. 1B is schematic view showing a state where a biological signal detection device is mounted in a vehicle.

FIG. 1B is a view showing a state where a biological signal detection device is mounted in a vehicle.

The electric field-type sensor 102 adapted to detect a biological signal is developed by the inventor of the present application (Japanese Patent Application No. 2013-217093). It is known that, as shown in FIG. 1A, although the electric field-type sensor 102 can detect a biological signal from a person-to-be-measured 103, the detectable distance is short; therefore, if the distance between the object-to-be-detected and the sensor increases, noise will become stronger, so that required biological signal cannot be detected.

On the other hand, compared to the electric field-type sensor 102, the commercially available Doppler sensor 101 has a function of detecting approaching or moving away of the person-to-be-measured 103 with longer detectable distance, but does not have a resolution high enough to detect the cardiopulmonary function of the person-to-be-measured 103. The inventor of the present invention has examined the output signal of the Doppler sensor 101, and found that the output signal of the Doppler sensor 101 is extremely similar to the noise component of the electric field-type sensor 102.

Thus, the inventor of the present invention thinks that it is possible to remove the noise by subtracting the output signal of the Doppler sensor 101 from the output signal of the electric field-type sensor 102 so as to increase the detectable distance, and attains the present invention after trial and error. Thus, the electric field-type sensor 102 and the Doppler sensor 101 are combined to each other to form a biological signal detection device 104, and the biological signal detection device 104 is mounted in a vehicle as shown in FIG. 1B, so that it becomes possible to detect the pulse and/or heart sound of the driver in a non-contact manner and with low noise. The pulse and/or heart sound of the driver detected by the biological signal detection device 104 can be used by an information system adapted to detect the health condition of the driver and issue a warning for preventing accidents.

[Overall Configuration of Biological Signal Detection Device 104]

Figure 2:
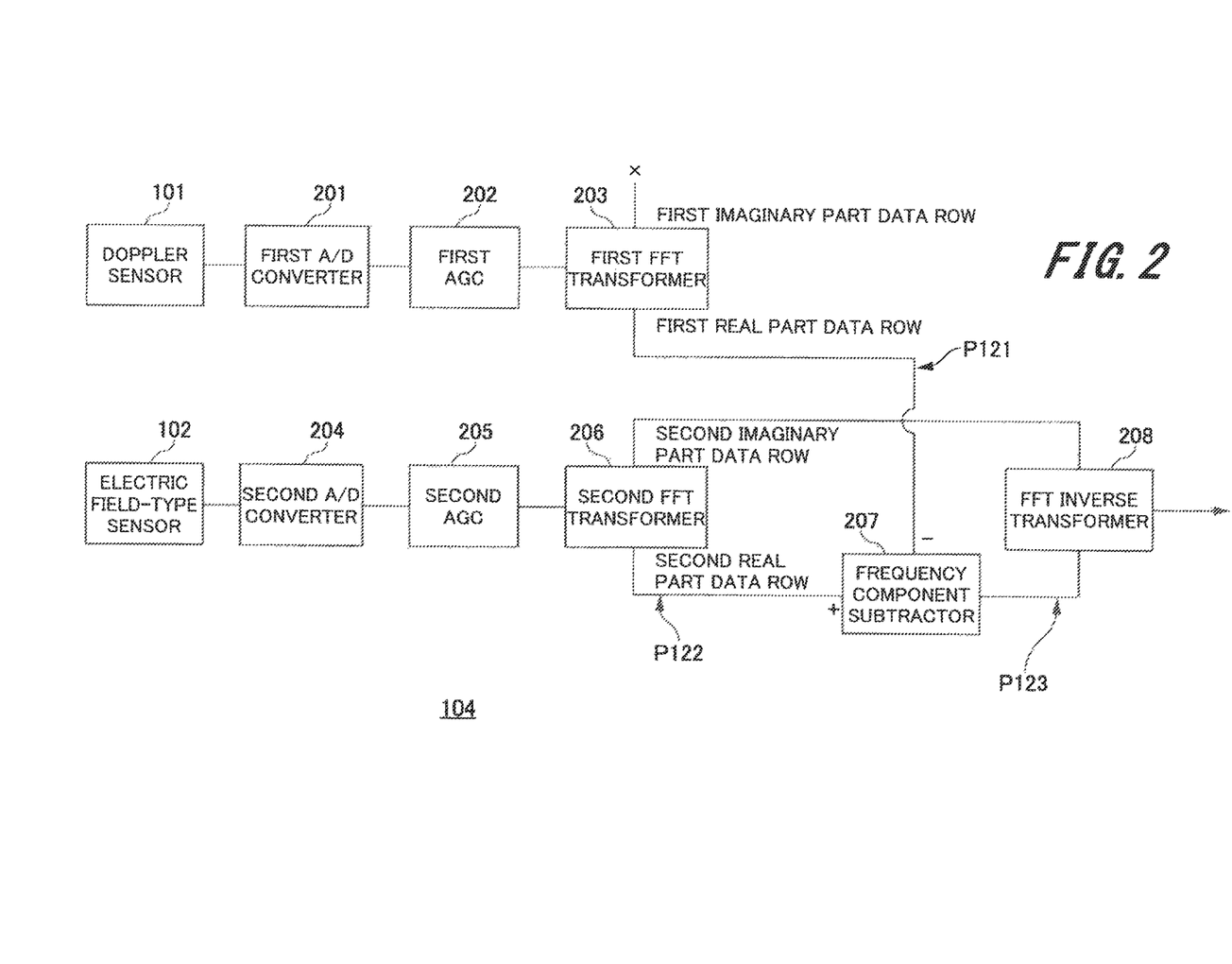
FIG. 2 is a block diagram of the biological signal detection device according to an embodiment of the present invention.

FIG. 2 is a block diagram of the biological signal detection device 104 according to an embodiment of the present invention.

An output signal of the Doppler sensor 101 is converted into digital data by a first A/D converter 201, and then the amplitude of the digital data is adjusted by a first AGC 202. Further, the signal outputted from the first AGC 202 is subjected to fast Fourier transformation processing performed by a first FFT transformer 203.

An output signal of the electric field-type sensor 102 is converted to digital data by a second A/D converter 204, and then the amplitude of the digital data is adjusted by a second AGC 205. Further, the signal outputted from the second AGC 205 is subjected to fast Fourier transformation processing performed by a second FFT transformer 206. Incidentally, a buffer (not shown) built in the first FFT transformer 203 and a buffer (not shown) built in the second FFT transformer 206 have the same memory capacity.

The first FFT transformer 203 outputs a first real part data row and a first imaginary part data row, both having number of elements equal to the memory capacity of the buffer.

Similar to the first FFT transformer 203, the second FFT transformer 206 also outputs a second real part data row and a second imaginary part data row, both having number of elements equal to the memory capacity of the buffer.

The second real part data row outputted from the second FFT transformer 206 and the first real part data row outputted from the first FFT transformer 203 are each supplied to a frequency component subtractor 207 where the second real part data row is subtracted from the first real part data row. In such a manner, the frequency component subtractor 207 outputs a noise-removed first real part data row.

A FFT inverse transformer 208 receives the noise-removed first real part data row and the second imaginary part data row, and performs a fast Fourier inverse transformation on the received data rows to output a noise-removed electric field-type sensor signal.

Incidentally, the first imaginary part data row outputted by the first FFT transformer 203 is discarded without being used for any other purpose.

[Overall Configuration of Electric Field-Type Sensor 102]

Figure 3:
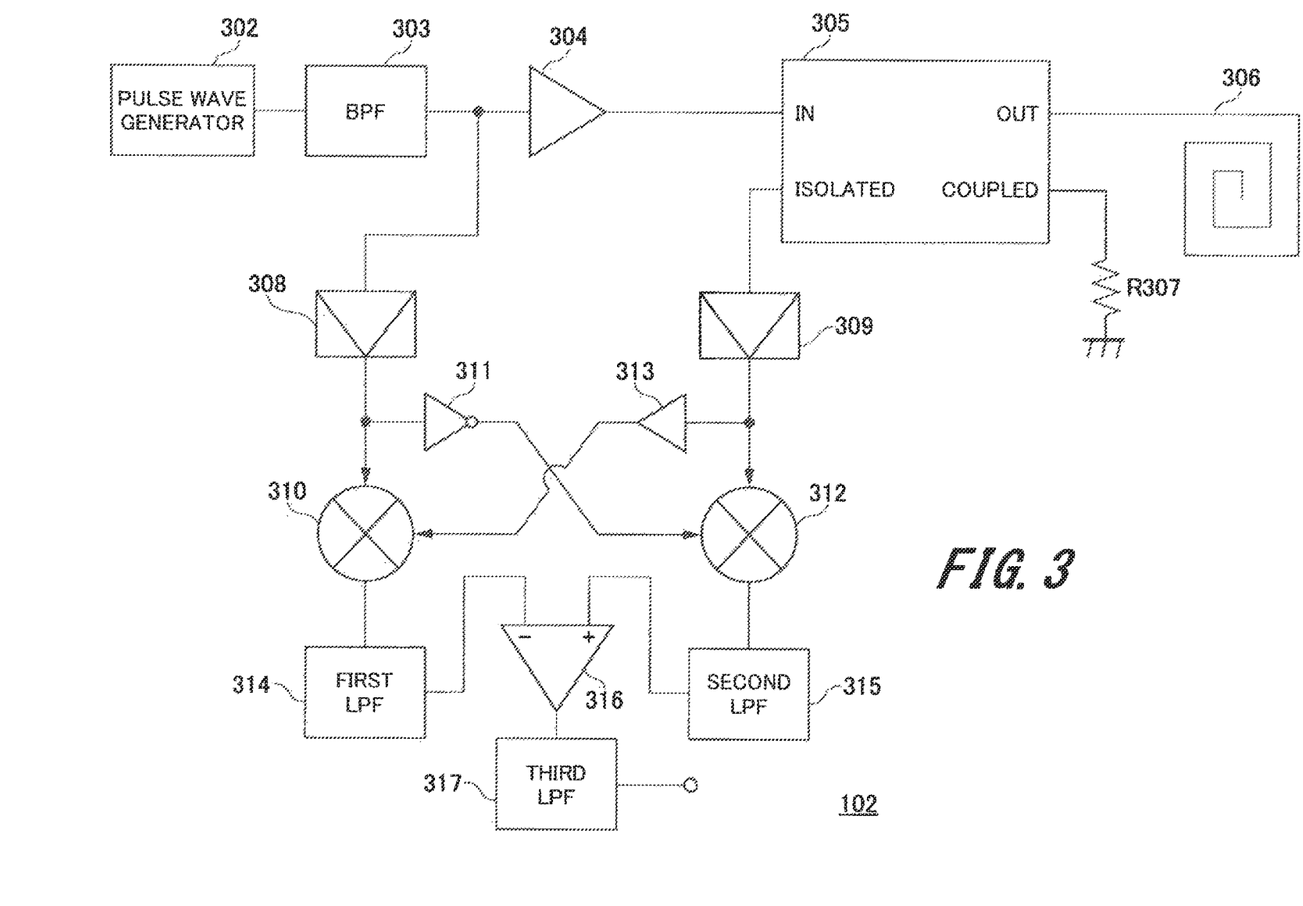
FIG. 3 is a block diagram of the electric field-type sensor.

FIG. 3 is a block diagram of the electric field-type sensor 102. The technical content of the electric field-type sensor 102 is disclosed in a patent application for a "pulse sensor" (JP2013-217093) which is filed by the inventor of the present application.

The electric field-type sensor 102 can be divided into the following two elements.

The first element is transmitting a radio wave (which is a traveling wave) to an object, and receiving and extracting a reflected wave reflected from the object. The first element includes a pulse wave generator 302, a BPF 303, a first RF amplifier 304, a directional coupler 305, and a helical antenna 306.

The second element is generating a frequency difference signal from the traveling wave and the reflected wave, and extracting the biological signal. The second element includes a second RF amplifier 308, a third RF amplifier 309, a first mixer 310, a second mixer 312, a first LPF 314, a second LPF 315, a differential amplifier 316, and a third LPF 317.

The pulse wave generator 302 (which may also be referred to as a "signal generator") generates a pulse having relatively low frequency. The frequency of the pulse generated by the pulse wave generator 302 is, for example, 1 MHz.

The BPF 303 extracts harmonic components from the pulse generated by the pulse wave generator 302. The central frequency and bandwidth of the BPF 303 is, for example, 60 MHz±3 MHz. For example, a circuit structure obtained by connecting multiple stages of LC resonance circuits can be used as the BPF 303.

The first RF amplifier 304 amplifies the signal of the harmonic components of the pulse passed through the BPF 303.

The signal of the harmonic components of the pulse having been amplified by the first RF amplifier 304 is inputted to an input terminal of the directional coupler 305 (the terminal indicated as "IN" in FIG. 3). Further, the signal of the harmonic components of the pulse is supplied to the helical antenna 306 connected to an output terminal of the directional coupler 305 (the terminal indicated as "OUT" in FIG. 3).

The directional coupler 305 is a widely known circuit element configured by a coil(s), a capacitor(s), and a resistor(s), and is used in a VSWR (Voltage Standing Wave Ratio) meter or the like. The directional coupler 305 can respectively output an output signal proportional to the traveling wave and an output signal proportional to the reflected wave based on the traveling wave and the reflected wave included in a first transmission path.

The helical antenna 306 emits a radio wave having a plurality of frequencies based on the signal of the harmonic components of the pulse. Further, the radio wave reflected by the object (such as a human body) is received by the helical antenna 306 to generate a standing wave in the directional coupler 305.

A signal proportional to the signal of the radio wave inputted from the output terminal of the directional coupler 305 through the helical antenna 306 (i.e., the reflected wave) is outputted to an insulated terminal of the directional coupler 305 (the terminal indicated as "INSULATED" in FIG. 3).

A signal proportional to the signal of the harmonic components of the pulse (i.e., the traveling wave) inputted to the input terminal of the directional coupler 305 is outputted to a coupling terminal of the directional coupler 305 (the terminal indicated as "COUPLED" in FIG. 3).

The coupling terminal is connected to a ground node through a resistor R307. The resistance of the resistor R307 is set to a value equal to the impedance of the directional coupler 305 or helical antenna 306. In most cases, the impedance of the directional coupler 305 or helical antenna 306 is 50Ω or 75Ω.

The second RF amplifier 308 amplifies the signal of the harmonic components of the pulse passed through the BPF 303 (i.e., the traveling wave).

The third RF amplifier 309 amplifies the signal of the radio wave (i.e., the reflected wave) inputted from the output terminal through the helical antenna 306 and outputted from the insulated terminal of the directional coupler 305.

The output signal of the second RF amplifier 308 is supplied to the second mixer 312 through an inverting amplifier 311, as well as being supplied to the first mixer 310.

The output signal of the third RF amplifier 309 is supplied to the first mixer 310 through a buffer 313, as well as being supplied to the second mixer 312. Incidentally, even if the phase of the output signal of the second RF amplifier 308 and the phase of the output signal of the third RF amplifier 309 are different from each other, a desired signal can be obtained from the first mixer 310 and the second mixer 312. Thus, a buffer (a non-inverting amplifier) can be used instead of the inverting amplifier 311.

Thus, the first mixer 310 and the second mixer 312 each output a multiplication signal of the traveling wave and the reflected wave. Here, a dual gate FET, for example, can be used as the first mixer 310 and the second mixer 312.

The output signal of the first mixer 310 is supplied to the first LPF 314. In the multiplication signal of the traveling wave and the reflected wave outputted from the first mixer 310, the first LPF 314 outputs a difference signal between the frequency of the traveling wave and the frequency of the reflected wave.

Similarly, the output signal of the second mixer 312 is supplied to the second LPF 315. In the multiplication signal of the traveling wave and the reflected wave outputted from the second mixer 312, the second LPF 315 outputs a difference signal between the frequency of the traveling wave and the frequency of the reflected wave.

The output signal of the first LPF 314 and the output signal of the second LPF 315 are inputted to the differential amplifier 316. The differential amplifier 316 (which is an operational amplifier) outputs a signal obtained by removing noise components from both the output signal of the first LPF 314 and the output signal of the second LPF 315.

The output signal of the differential amplifier 316 is supplied to the third LPF 317. The third LPF 317 removes AC components having relatively high frequency from the output signal of the differential amplifier 316, and passes through a low frequency signal indicating the biological signal of the human body.

[Operation of Electric Field-Type Sensor 102]

The operation of the electric field-type sensor 102 will be described below with reference to FIG. 4A, FIG. 4B, FIG. 4C, FIG. 4D, FIG. 5A and FIG. 5B.

Figure 4A:
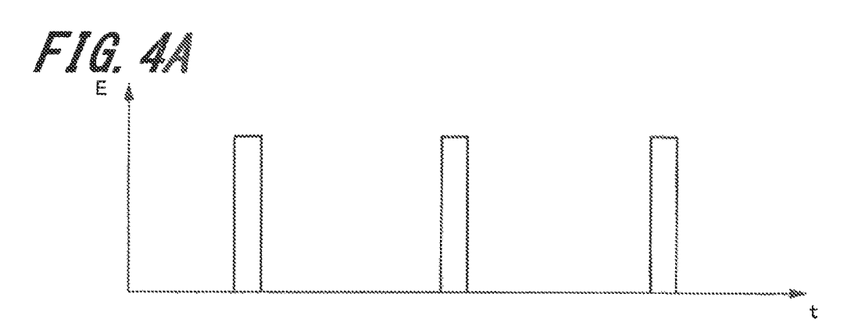
FIG. 4A shows a waveform diagram of the pulse outputted by a pulse wave generator.

FIG. 4A shows a waveform diagram of the pulse outputted by the pulse wave generator 302. In the waveform diagram shown in FIG. 4A, the horizontal axis represents time, and the vertical axis represents voltage. As shown in FIG. 4A, since a waveform having small duty ratio and close to impulse includes much harmonic wave, such waveform is preferred for the electric field-type sensor 102 of the present embodiment.

Figure 4B:
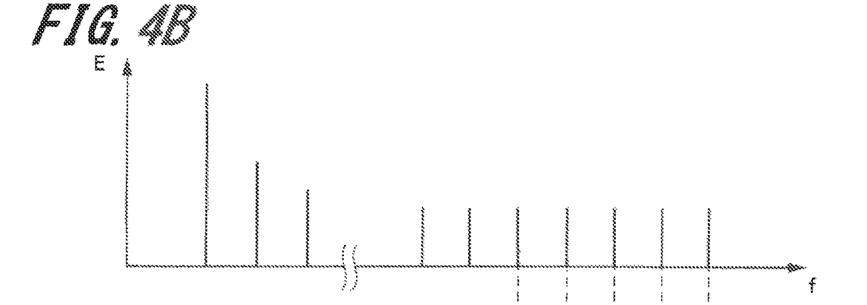
FIG. 4B shows a spectrum of frequency components obtained by performing a Fourier transformation on the pulse outputted by the pulse wave generator, in a frequency domain.

FIG. 4B shows a spectrum of frequency components obtained by performing a Fourier transformation on the pulse shown in FIG. 4A and outputted by the pulse wave generator 302, in a frequency domain. In the spectrum shown in FIG. 4B, the horizontal axis represents frequency, and the vertical axis represents voltage. As shown in FIG. 4B, the pulse includes a plurality of harmonic waves, each having a frequency equal to an integral multiple of that of the fundamental wave.

Figure 4C:
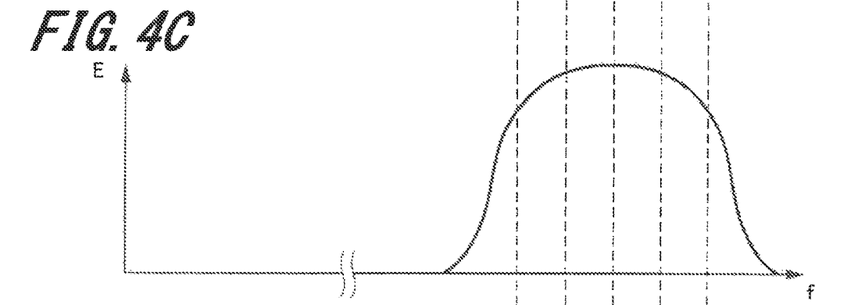
FIG. 4C shows a frequency characteristic chart of a BPF.

FIG. 4C is a frequency characteristic chart of the BPF 303. Since the scale of FIG. 4C is matched to that of the FIG. 4B, the horizontal axis of the frequency characteristic chart represents frequency, and the vertical axis of the frequency characteristic chart represents voltage.

Figure 4D:
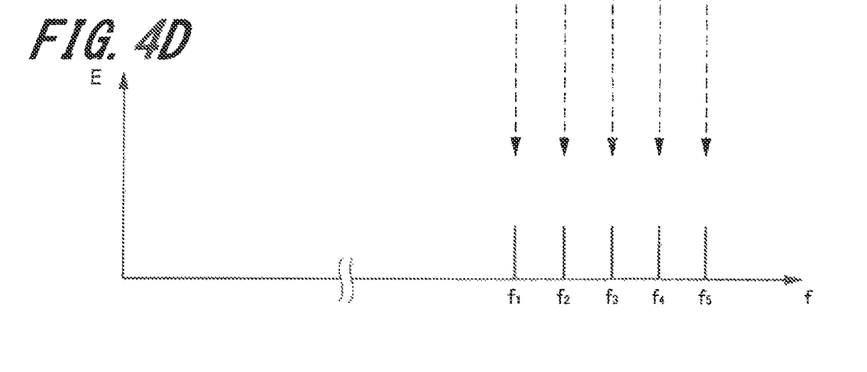
FIG. 4D shows a spectrum of harmonic components passing through the BPF.

FIG. 4D is a frequency distribution chart of the signal passing through the BPF 303. Since the scale of FIG. 4D is matched to that of the FIG. 4C, the horizontal axis of the frequency characteristic chart represents frequency, and the vertical axis of the frequency characteristic chart represents voltage.

As shown in FIG. 4C, among the harmonic components contained in the pulse, the BPF 303 causes components having specified frequencies to pass therethrough. As a result, as shown in the frequency distribution chart of FIG. 4D, the harmonic components passed through the BPF 303 are obtained by removing frequency components equal to or less than a cutoff frequency (including the fundamental wave) from the pulse.

Figure 5A:
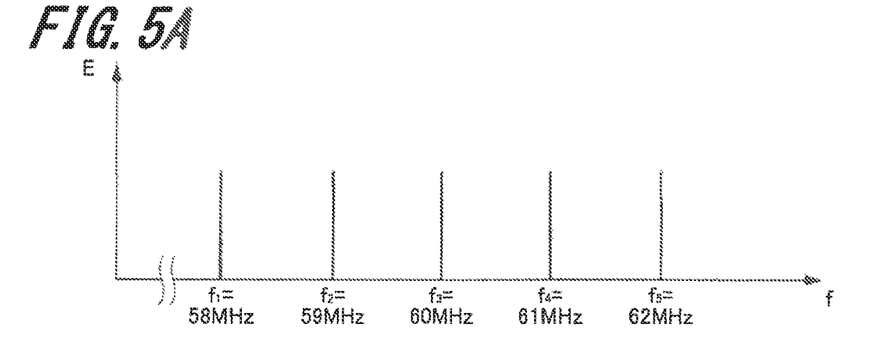
FIG. 5A is a spectrum showing the harmonic components passed through the BPF.

FIG. 5A shows a spectrum obtained by enlarging the frequency axis (the horizontal axis) of the frequency distribution chart of FIG. 4D; the spectrum shown in FIG. 5A indicates the harmonic components passed through the BPF 303.

Figure 5B:
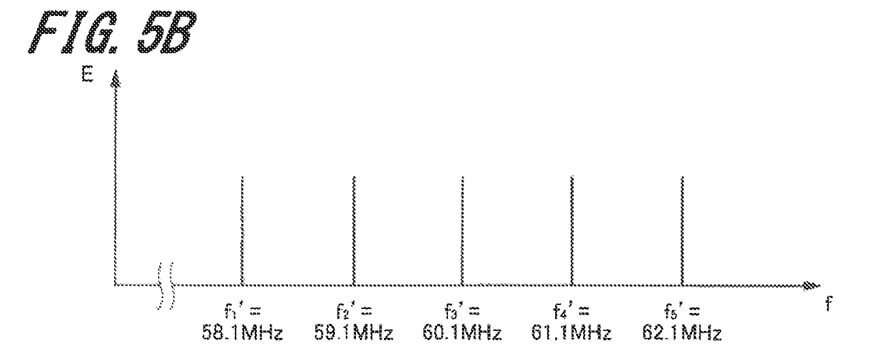
FIG. 5B is a spectrum showing a reflected wave outputted from a directional coupler.

FIG. 5B shows a spectrum of the reflected wave outputted from the directional coupler 305.

Here, as shown in FIG. 5A, the harmonic components passed through the BPF 303 are five signals with a signal having a frequency of 60 MHz as the center. The frequencies of the five signals are, in ascending order of frequency: $f_1$=58 MHz, $f_2$=59 MHz, $f_3$=60 MHz, $f_4$=61 MHz, $f_5$=62 MHz. Such five signals are amplified by the first RF amplifier 304, and emitted as radio waves from the helical antenna 306 through the directional coupler 305.

However, since the frequency characteristic (bandwidth) of the helical antenna 306 is narrow, among the live signals of $f_1$ to $f_5$, only one or two signals are emitted as a radio wave from the helical antenna 306.

Further, the radio wave emitted from the helical antenna 306 is reflected by the object, and inputted to the directional coupler 305 through the helical antenna 306. Such reflected wave signal is any one of the following, in ascending order of frequency: $f_1'$=58.1 MHz, $f_2'$=59.1 MHz, $f_3'$=60.1 MHz, $f_4'$=61.1 MHz, $f_5'$=62.1 MHz, as shown in FIG. 5B. In such example, because of Doppler effect, the frequency of the reflected wave is shifted from that of the traveling wave by 100 kHz.

Any one of $f_1$-$f_5$ and any one of $f_1'$-$f_5'$ are inputted to the first mixer 310 and the second mixer 312 where multiplication is performed. Thus, a signal obtained by summing respective frequencies and a signal obtained by performing subtraction between respective frequencies are outputted from the first mixer 310 and the second mixer 312.

For example, in the case where the reflected wave is $f_1'$, the signal obtained by summing respective frequencies will be $f_1+f_1'$, $f_2+f_1'$ . . . . $f_5+f_1'$.

In the case where the reflected wave is $f_2'$, the signal obtained by summing respective frequencies will be $f_1+f_2'$, $f_2+f_2'$ . . . $f_5+f_2'$.

The same goes for the case where the reflected wave is $f_3'$, the case where the reflected wave is $f_4'$, and the case where the reflected wave is $f_5'$. For example, in the case where the reflected wave is $f_5'$, the signal obtained by summing respective frequencies will be $f_1+f_5'$, $f_2+f_5'$ ... $f_5+f_5'$.

For example, in the case where the reflected wave is $f_1'$, the signal obtained by performing subtraction between respective frequencies will be $|f_1-f_1'|$, $|f_2-f_1'|$ ... $|f_5-f_1'|$.

In the case where the reflected wave is $f_2'$, the signal obtained by performing subtraction between respective frequencies will be $|f_1-f_2'|$, $|f_2-f_2'|$ ... $|f_5-f_2'|$.

The same goes for the case where the reflected wave is $f_3'$, the case where the reflected wave is $f_4'$, and the case where the reflected wave is $f_5'$. For example, in the case where the reflected wave is $f_5'$, the signal obtained by performing subtraction between respective frequencies will be $|f_1-f_5'|$, $|f_2-f_5'|$ ... $|f_5-f_5'|$.

Among the signals outputted from the first mixer 310 and the second mixer 312, the signals having the lowest frequency are $|f_1-f_1'|$, $|f_2-f_2'|$, $|f_3-f_3'|$, $|f_4-f_4'|$, and $|f_5-f_5'|$. In the case shown in FIG. 5A and FIG. 5B, the frequencies of these signals are all 100 kHz. These signals are only the components obtained by shifting the frequencies due to Doppler effect, and all these signals have the same frequency.

If the object is located close to the antenna, the resonant frequency of the antenna will easily fluctuate corresponding to the position and movement of the object. Thus, even if a radio wave is emitted from the antenna by a single frequency, a mismatch will be created between the signal and the resonant frequency of the antenna, so that the reflected wave cannot be correctly received.

To solve such problem, in the vibration sensor of the embodiment of the present invention, a band-pass filter that contains the fluctuation of the resonant frequency is employed to use a plurality of radio waves each having a different frequency. With such a configuration, among the plurality of signals each having a different frequency, any one or two signals will match the bandwidth even when the resonant frequency of the antenna fluctuates, so that the reflected wave can be received.

If the reflected wave can be received, it will be possible to detect the existence and/or fluctuation state of the object by extracting, with a mixer, the frequency difference between the reflected wave and the traveling wave caused by Doppler effect.

Incidentally, 60 MHz is a frequency said to be most easy to be matched with the blood flow of the human body.

The electric field-type sensor 102 uses the differential amplifier 316 to remove the noise having in-phase components contained in the signal. Further, the noise having high-frequency components is also removed by being passed through the third LPF 317. After removing such noises, the electric field-type sensor 102 of the present embodiment can detect the biological signal of the person-to-be-measured 103 based on the weak fluctuation carried on the radio wave by the vibration of the person-to-be-measured 103, without using expensive equipment such as a fast Fourier transformer.

[Overall Configuration of Doppler Sensor 101]

Figure 6:
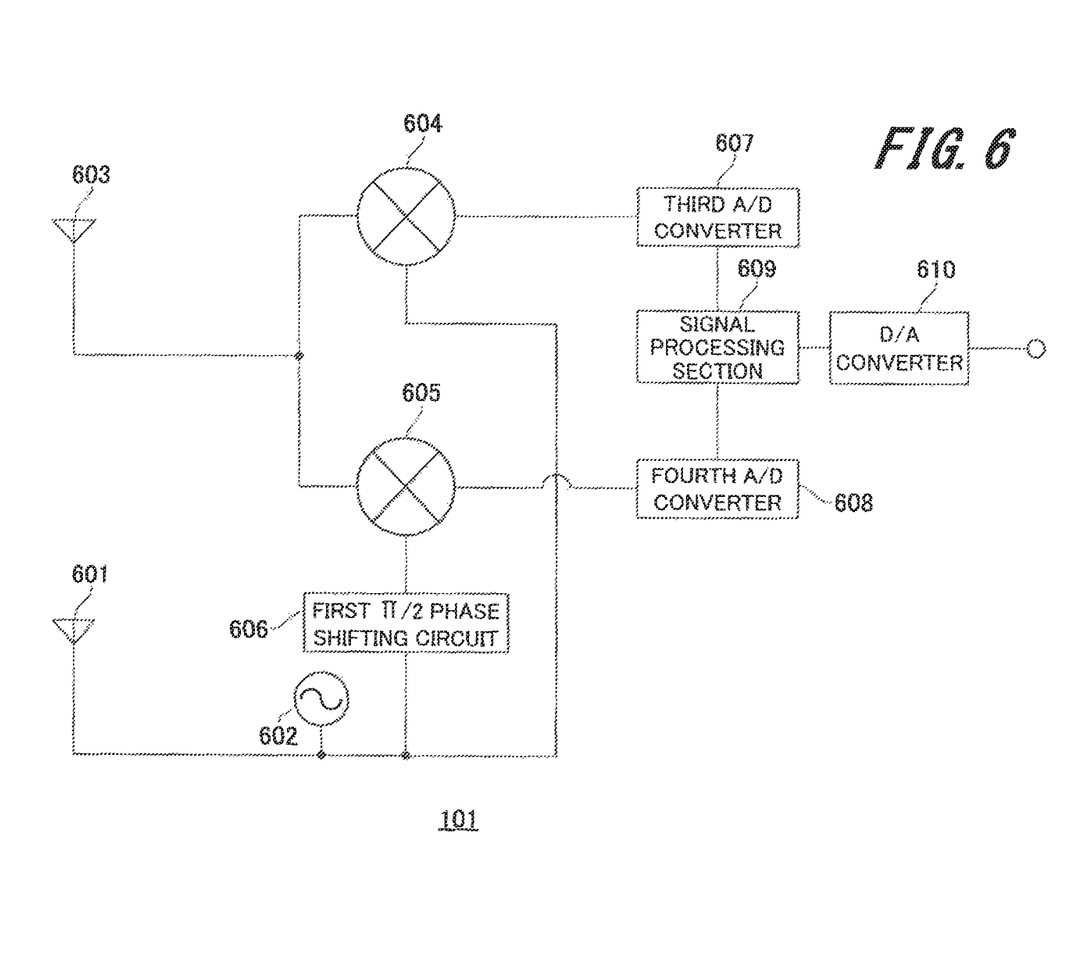
FIG. 6 is a block diagram of the Doppler sensor.

FIG. 6 is a block diagram of the Doppler sensor 101. The Doppler sensor 101 includes various implementations, and FIG. 6 shows one of the various implementations.

An oscillation source 602 is connected to a transmitting antenna 601, and the transmitting antenna 601 transmits a signal generated by the oscillation source 602 as a radio wave. The oscillation source 602 generates an ultra-high frequency signal of about 10 GHz. The radio wave is reflected by the object, and received by a receiving antenna 603. A third mixer 604 and a fourth mixer 605 are connected to the receiving antenna 603.

The third mixer 604 performs multiplication processing between the signal of the radio wave received from the receiving antenna 603 and the signal of the oscillation source 602.

The third mixer 605 performs multiplication processing between the signal of the radio wave received from the receiving antenna 603 and a signal obtained by delaying the signal of the oscillation source 602 by $\pi/2$ by a first $\pi/2$ phase shifting circuit 606.

A frequency difference component between the signal of the radio wave received from the receiving antenna 603 and the signal of the oscillation source 602 is outputted from the third mixer 604. Since the frequency of the signal outputted from the oscillation source 602 is too high, a frequency sum component will naturally decay by distribution constant in the circuit without particularly providing a LPF, and therefore will not be outputted as a significant signal.

Similar to the third mixer 604, a frequency difference component between the signal of the radio wave received from the receiving antenna 603 and the signal obtained by delaying the signal of the oscillation source 602 by $\pi/2$ by the first $\pi/2$ phase shifting circuit 606 is outputted from the fourth mixer 605. Similar to the third mixer 604, a frequency sum component does not appear in the fourth mixer 605.

The output signal of the third mixer 604 is converted into a digital signal by a third A/D converter 607. The output signal of the fourth mixer 605 is converted into a digital signal by a fourth A/D converter 608. The output data of the third A/D converter 607 and the output data of the fourth A/D converter 608 are subjected to a predetermined arithmetic processing performed by a signal processing section 609 (which is a microcomputer), and a signal equivalent to the movement of the object is outputted by a D/A converter 610.

[Operation of Biological Signal Detection Device 104]

Figure 7:
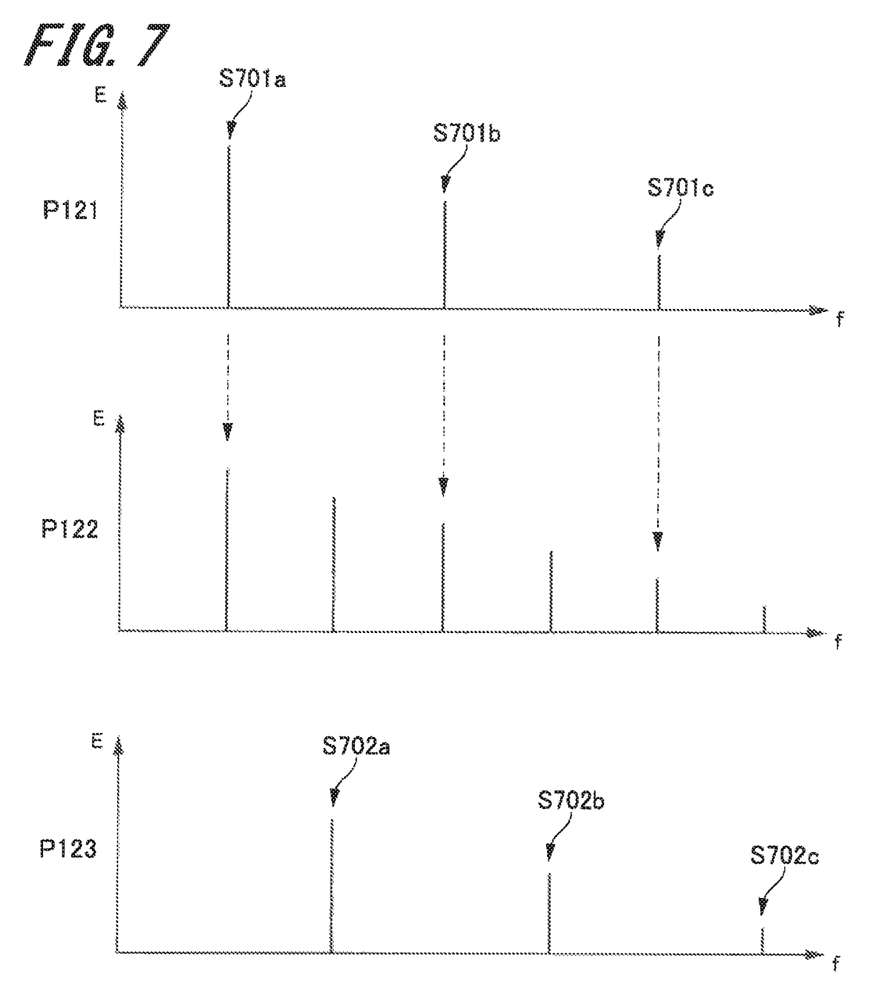
FIG. 7 is a schematic view showing the frequency component of each component of the biological signal detection device.

FIG. 7 is a schematic view showing the frequency component of each component of the biological signal detection device 104. In each graph of FIG. 7, the horizontal axis represents frequency, and the vertical axis represents voltage or signal level.

The first real part data row based on the output signal of the Doppler sensor 101 is the graph of P121. In the graph of P121, the signal component of the Doppler sensor 101 is composed of noise components S701a, S701b and S701c.

The second real part data row based on the output signal of the electric field-type sensor 102 is the graph of P122. Of the first real part data row and the second real part data row, if the first real part data row is subtracted from the second real part data row, both having the same frequency component, the result will be a noise-removed first real part data row of P123. In the graph of P123, the signal component of the noise-removed first real part data row is composed of biological signal components S702a, S702b and S702c. In other words, the second real part data row based on the output signal of the electric field-type sensor 102 is composed of the noise components S701a, S701b and S701c and the biological signal components S702a, S702b and S702c.

The embodiments described above include the following applications.

(1) In the electric field-type sensor 102, the helical antenna 306 is used; however, various other antennas can be used instead of being limited to the helical antenna 306. For example, other antennas, such as a dipole antenna, a ground plane antenna, a meander line antenna and the like, can be used as long as the antenna has an open end. Further, a loop antenna which has no open end can also be used, though gain will be reduced.

(2) Alternatively, a circuit that generates a white noise may be used instead of the pulse wave generator 302.

(3) Since commercially available Doppler sensor 101 is adapted to function as a human sensor, there exists a case where the Doppler sensor 101 does not include the D/A converter 610, and a logic signal is outputted by a comparator. In such a case, it is possible to directly extract the digital data from a microcomputer constituting the Doppler sensor 101, and supply the extracted the digital data to the first AGC 202.

The biological signal detection device 104 obtained by combining the Doppler sensor 101 with the biological signal detection device 104 has been described in the aforesaid embodiment.

It is possible to remove the noise of the electric field-type sensor 102 by using the output signal of the Doppler sensor 101 to subtract the frequency component of the Doppler sensor 101 from the first real part data row obtained by performing fast Fourier transformation, with respect to the output signal of the electric field-type sensor 102, which is susceptible to the effect of noise due to having a low sensitivity to distance.

The embodiment of the present invention are described as above; however, it is to be understood that the present invention is not limited to the embodiment described above, and various modifications and applications can be made without departing from the spirit described in the claims of the present invention.

For example, in the aforesaid embodiments, the configurations of the device and system are described in detail and concrete manner so that the present invention is easily understandable; however, the aforesaid configurations do not have to be fully included. Further, configurations of one embodiment can be partly substituted with configurations of another embodiment, and configurations of one embodiment can be added to a configuration(s) of another embodiment. Further, configurations of one embodiment can be partly omitted, or added with other configuration(s), or substituted with other configurations.

Further, the aforesaid each configuration, function, processor and the like can be partly or entirely achieved by hardware by being designed using an integrated circuit, for example. Further, the aforesaid each configuration, function and the like can be achieved by software whose processor explains and executes a program that achieves respective functions. Information such as the program, tables, files and the like for achieving each function can be stored in a volatile or non-volatile storage, such as a memory, a hard disk, a SSD (solid state drive) or the like, or a recording medium, such as an IC card, an optical disk or the like.

Further, a control line and an information line are shown because it is required for description, but the product does not necessarily show the control line and information line. It can be considered that almost all configurations are actually connected with each other.

REFERENCE SIGNS LIST

101 Doppler sensor
102 electric field-type sensor
103 person-to-be-measured
104 biological signal detection device
201 first A/D converter
202 first AGC
203 first FFT transformer
204 second A/D converter
205 second AGC
206 second FFT transformer
207 frequency component subtractor
208 FFT inverse transformer
302 pulse wave generator
303 BPF
304 first RF amplifier
305 directional coupler
306 helical antenna
308 second RF amplifier
309 third RF amplifier
310 first mixer
311 inverting amplifier
312 second mixer
313 buffer
314 first LPF
315 second LPF
316 differential amplifier
317 third LPF
601 transmitting antenna
602 oscillation source
603 receiving antenna
604 third mixer
605 fourth mixer
606 first π/2 phase shifting circuit
607 third A/D converter
608 fourth A/D converter
609 signal processing section
610 D/A converter

The invention claimed is:

1. A biological signal detection device comprising:
a first FFT transformer that performs fast Fourier transformation on a signal of a first sensor, and that outputs a complex data row formed by a first real part data row and a first imaginary part data row;
a second FFT transformer that performs fast Fourier transformation on a signal of a second sensor, and that outputs a complex data row formed by a second real part data row and a second imaginary part data row;
a frequency component subtractor that subtracts the first real part data row from the second real part data row to output a noise-removed first real part data row; and
a FFT inverse transformer that performs fast Fourier inverse transformation on the noise-removed first real part data row and the second imaginary part data row.

2. The biological signal detection device according to claim 1,
wherein the first sensor is a Doppler sensor, and
wherein the second sensor is an electric field-type sensor that detects variation in impedance of a human body, which is a person-to-be-measured, as a biological signal.

* * * * *